Figure 4:
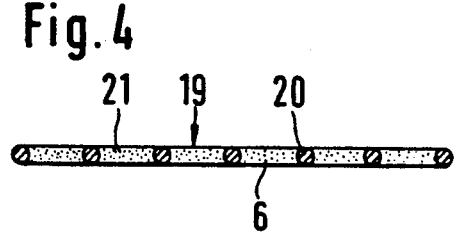

United States Patent
Plesch et al.

[11] Patent Number: 5,290,515
[45] Date of Patent: Mar. 1, 1994

[54] METHOD FOR THE MANUFACTURE OF A SELF-SUPPORTING TEST FIELD MATERIAL

[75] Inventors: Winfried Plesch, Dossenheim; Dan Mosoiu, Limburgerhof; Hans Götschel, Mannheim, all of Fed. Rep. of Germany

[73] Assignee: Boehringer Mannheim GmbH, Mannheim, Fed. Rep. of Germany

[21] Appl. No.: 937,877

[22] PCT Filed: Feb. 27, 1992

[86] PCT No.: PCT/DE92/00160
§ 371 Date: Oct. 20, 1992
§ 102(e) Date: Oct. 20, 1992

[87] PCT Pub. No.: WO92/15880
PCT Pub. Date: Sep. 17, 1992

[30] Foreign Application Priority Data
Feb. 28, 1991 [DE] Fed. Rep. of Germany ....... 4106293
Jun. 24, 1991 [DE] Fed. Rep. of Germany ....... 4120823

[51] Int. Cl.$^5$ .................... G01N 31/22; B05D 1/26; B05D 3/00
[52] U.S. Cl. .......................... 422/57; 422/58; 427/2; 427/358; 427/389.9; 427/420; 427/434.2
[58] Field of Search .................... 422/56–58; 427/2, 358, 389.9, 420, 434.2

[56] References Cited

U.S. PATENT DOCUMENTS

| | | | |
|---|---|---|---|
| 4,292,272 | 9/1981 | Kitajuma et al. | 422/57 |
| 4,588,614 | 5/1986 | Lauchenauer | 427/358 |
| 4,604,264 | 8/1986 | Rothe et al. | 422/56 |

FOREIGN PATENT DOCUMENTS

| | | |
|---|---|---|
| 0073056 | 3/1983 | European Pat. Off. |
| 0246505 | 11/1987 | European Pat. Off. |
| 0297390 | 1/1989 | European Pat. Off. |
| 0302287 | 2/1989 | European Pat. Off. |

*Primary Examiner*—Jill A. Johnston
*Attorney, Agent, or Firm*—Nikaido, Marmelstein, Murray & Oram

[57] ABSTRACT

Method for the manufacture of a self-supporting test field material of very small layer thickness. In a strip of test material (1) comprising an open-pored fibre structure a reagent film mass (6) is embedded from an application side (1a) in such a way that it extensively penetrates into the pores of the carrier material. The reagent film mass (6) is smoothed on the opposite side (1b) by the relative motion of the ribbon and a smoothing tool (4) in such a way that the pores of the composite fibre structure are spanned by the reagent film mass (6). Finally, the carrier material ribbon (10) thus produced is dried essentially free of contact.

19 Claims, 2 Drawing Sheets

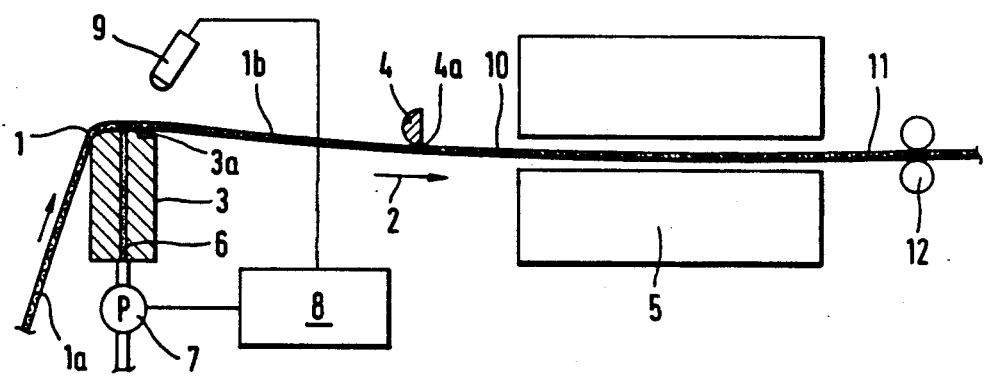
Fig. 1
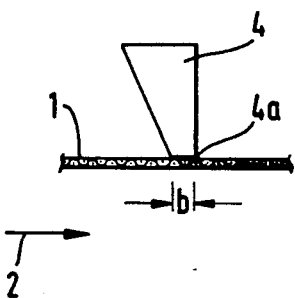
Fig. 2
Fig. 3
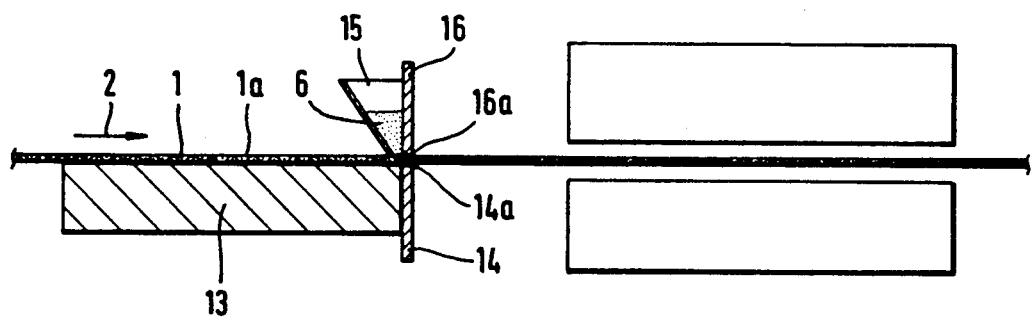

METHOD FOR THE MANUFACTURE OF A SELF-SUPPORTING TEST FIELD MATERIAL

The invention relates to a method for the manufacture of a self-supporting test field material of very small layer thickness and to such a test field material.

For the quantitative and/or qualitative analytical determination of constituents of body fluids, especially blood and urine, so-called carrier-bound tests are increasingly being used. In these, a reagent system is embedded in at least one single-layer or multi-layer test field of a test carrier (in the English-language literature frequently also called "solid reagent analysis element"), said test field being placed in contact with the sample. The reaction of sample and reagent leads to an optically or otherwise detectable change, which can be evaluated visually or by means of an instrument (usually by reflection photometry).

The layer thickness of the test field materials used is very important for the quality of the analysis. In general, a layer thickness as thin as possible is aimed for. An intense colour formation, extremely important for the accuracy of the analysis, can thereby be achieved with a small quantity of reagents. Layer thinness furthermore reduces the quantity of sample fluid required. This is particularly important when, with the use of modern analytical methods, a plurality of analyses are to be performed on a single drop of blood (obtained by pricking the finger).

For this reason thin reagent films, in some cases less than 0.1 mm thick, are often used. They are manufactured in a layer-forming method by applying a film-forming mass (reagent film mass) to a carrier layer (usually a transparent plastic film). The reagent film mass is based on a dispersion or solution of a polymeric film former and contains the reagents required in the respective test layer.

In general, such reagent films are produced in the test carrier together with the carrier material (for example set in a frame or bonded on to a strip-type base layer). Removal of the film layer from the carrier film on which it was formed has also been described. However, with the use of thin films this is not feasible in practice.

There is therefore a need for a test material of extreme thinness (less than 0.1 mm thick) which is suitable as a self-supporting test field material, i.e. which can be used without connection with a carrier layer over the whole area.

A test field material within the meaning of the present invention is any thin, flat structure which as a separate component can be integrated into the test field of a test carrier. The test field may consist exclusively of this test field material. There may also be used a plurality of test field materials according to the invention or combinations with other layer materials commonly employed in test carrier technology, for example paper, plastic membranes or fibre materials.

The aim of the invention is to provide a test field material which, with extreme layer thinness, has self-supporting properties and fulfils the additional stringent requirements in the field of body fluid analysis.

To achieve this aim, in a method of the kind described in the preamble it is proposed that a reagent film mass be pressed from an application side into a carrier material ribbon consisting of an open-pored fibre structure in such a way that it penetrates extensively into the pores of the carrier material, the impregnating mass on the opposite side is smoothed by the relative motion of the ribbon and a smoothing tool in such a way that the pores of the composite fibre structure are spanned by the reagent film mass and the ribbon of test field material thus produced is dried without contact.

The term "open pored fibre structure" signifies any type of textile structure of fibres or threads to create a thin, open-pored layer. Examples are woven or knitted fabric and mats. The use of a single-layer woven or knitted fabric, preferably consisting of monofilamentous threads, has proved especially successful. The mean pore width of the composite fibre structure should be between 0.02 mm and 0.08 mm, preferably between 0.03 mm and 0.05 mm.

The composition of the reagent film mass essentially depends on the function of the test field material according to the invention in the respective test carrier. It contains, apart from a dispersed or dissolved polymeric film former, the reagent components necessary for the respective test (e.g. enzymes, substrates and buffer reagents) and auxiliary materials, for example, pigment or pulping components. In any case, the viscosity of the reagent film mass at the time of impregnation of the carrier material should be between 10 and 300 mPasec, preferably between 20 and 200 mPasec.

Another article of the invention is a test field material for a test carrier for the determination of an analyte in a body fluid, said test field material incorporating an open-pored fibre structure in which a reagent film material is embedded in such a way that it spans, and thus closes, its pores, the reagent film material being formed of a film-forming, viscous reagent film mass which is pressed into the fibre structure and is smoothed on both sides, so that the reagent film material is distributed essentially symmetrically over the layer thickness of the test field material.

The use of a combination of a fibre layer with a reagent film is known from the U.S. Pat. Nos. 4,292,272 and 4,604,264. In the former, a film-forming mass is applied to a plastic film and the tissue is pressed into the still moist mass. The tissue serves here primarily to spread the sample over the surface of the test field (so-called "spreading layer"). This method is unsuitable for manufacturing an extremely thin, self-supporting test layer. The film-forming mass is located mainly on one side of the tissue, i.e. it is asymmetrically distributed. In U.S. Pat. No. 4,604,264, a film-forming mass containing reagents is applied to a tissue layer purposefully so that it remains mainly on one side of the layer, i.e. an asymmetrical layer structure results. This is deemed necessary in order to guarantee good optical properties of the layer.

The composite fibre structure preferably consists of monofilamentous threads. According to the invention, an extremely thin test field material with uniform distribution of the reagent film mass is produced in a single operation. In practice, for example, a test field material has been manufactured which is some 0.06 mm thick and according to layer thickness measurement, content analysis and function testing has very good properties. In U.S. Pat. No. 4,604,264 a monofilamentous tissue is regarded as less advisable and is used only in connection with an additional carrier film. Uniform properties, hence suitable for test purposes, are here achieved only with relatively large layer thicknesses. This results in a high reagent consumption and long reaction times.

The use of reagent-impregnated tissues or mats as test field materials is also known. However, these differ fundamentally from the test field material of the present invention in respect of both manufacturing method and structure. In the known methods, impregnation generally occurs in that a ribbon of tissue is guided through an impregnating tank containing a comparatively highly fluid impregnating solution with the reagents and any other auxiliary substances. The ribbon is guided from the tank and the excess impregnating solution wiped off while transporting the ribbon vertically so that the excess can flow back into the tank. The impregnated tissue retains its open-pore characteristic. The process therefore does not involve a closed layer, in which the pores of the tissue are spanned by a relatively highly viscous reagent film mass. In the context of the present invention it was established that the known method does not yield a satisfactory result even when the viscosity of the impregnating solution in the tank is increased to such an extent that it closes the pores of the tissue. Rather, an uneven distribution of the reagent film mass occurs.

Figure 5:
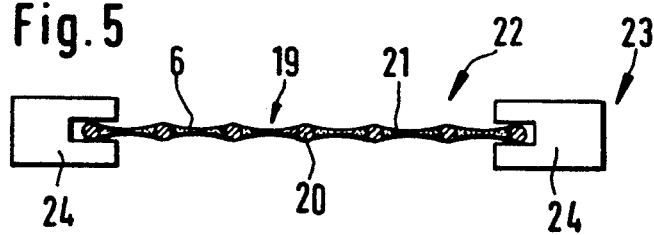
Figure 6:
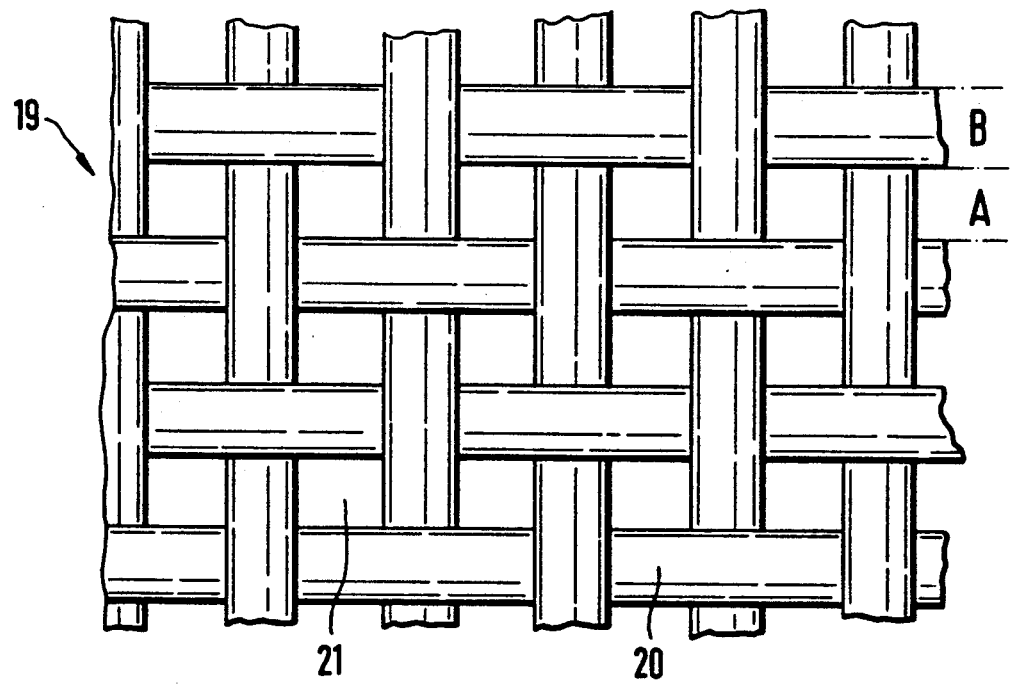

The invention will be explained in detail below by means of an exemplifying embodiment represented diagrammatically in the following figures:

FIG. 1 A highly diagrammatic side view of an first system for performing the method according to the invention;

FIG. 2 A detailed view of a modified embodiment;

FIG. 3 A side view of an alternative embodiment of a system for performing the method according to the invention, analogous to FIG. 1;

FIG. 4 A section through a test field material according to the invention before drying;

FIG. 5 A section through a test carrier with a test field material according to the invention;

FIG. 6 A top view of a composite fibre structure suitable for the invention.

In the system shown in FIG. 1, a carrier material ribbon 1 is guided in the direction of the arrow 2 in succession via a slit orifice 3, beneath a smoothing tool 4 and through a drying chamber 5.

The slit orifice 3 and the smoothing tool 4 extend with the profile shown (perpendicularly to the plane of the drawing), over the whole width of the carrier material ribbon 1. Through slit orifice 3, a reagent film mass 6 is pressed into the carrier material ribbon 1 in such a way that the reagent film mass extensively penetrates into the pores of the open-pored fibre structure. In this case the application side 1a is the underside of carrier material ribbon 1.

On the opposite side 1b, the reagent film mass is smoothed by means of the smoothing tool 4 in such a way that the pores of the composite fibre structure are spanned by the reagent film mass and the threads of the carrier material ribbon are also covered (extremely thinly) with reagent film mass.

The reagent film mass 6 is supplied from a storage container (not shown) by means of a metering pump 7. Metering is controlled by a controller 8, which can optionally be connected to an actual-value indicator 9 which (for example by image analysis methods) monitors the penetration of the reagent film mass 6 into the carrier material ribbon 1.

Exact metering of the reagent film mass is essential for the quality of the result. On the one hand, the feed quantity must be at least large enough to penetrate into the open-pored fibre structure sufficiently far to allow its smoothing on the opposite side in such a way that the pores of the carrier material ribbon are completely closed. On the other hand, however, over-metering is also disadvantageous. The quantity of reagent film mass supplied is preferably limited so that no excess is wiped off during smoothing.

In practice it has proved sufficient to determine empirically the metering rate at which the reagent film mass 6 is fed and to manufacture the test field material continuously at this fixed metering rate. The possibility of regulation with the aid of an actual-value indicator 9, as shown in FIG. 1, should therefore be regarded as an additional option.

It is also essential that the test material 10, which after passage of the smoothing tool 4 is finished though still moist, be dried essentially without contact. It is preferably conveyed freely suspended through the drying chamber 5, as shown. The dried test field material 11 is drawn off by transport rollers 12 and wound on to a roller which is not shown. The still moist strip of test field material 10 can, of course, be touched by guide elements in confined area sections (especially at the edge), as long as this contact is so slight that its properties are not impaired as a result, or as long as the corresponding parts of the dried strip of test field material 11 are cut off and not used. "Essentially without contact" is to be understood in this sense.

As a smoothing tool 4 within the meaning of the invention should be regarded any machine element which extends over the width of the carrier material ribbon 1 and is suitable for smoothing the reagent film mass, which penetrates from the opposite side into the composite fibre structure. It is preferably fashioned—as shown—so that at the end rearward in the transport direction 2 it has an edge 4a, which touches the carrier material ribbon 1 and serves as a sharp edge. In this way a smooth stroke is obtained. Ahead of the sharp edge 4a, the surface of the smoothing tool 4 facing the carrier material 1 can be (as shown in FIG. 1) convexly curved or (as shown in FIG. 2) flat. It has been found that the so-called "doctor width", that is, the width b of the lower surface (sole) of the smoothing tool, which is in contact with the carrier material 1, should be relatively small. It is preferably less than 20 mm, and especially preferably less than 10 mm.

The slit orifice 3 preferably also has a sharp edge 3a, in order to produce a smooth surface on the application side 1a e also.

The above description should not be understood as meaning that the reagent film mass 6 is necessarily fed only on one side of the carrier material ribbon 1 and that a smoothing tool 4 is provided only on the other side. This is in general expedient and economical. However, the scope of the invention is not exceeded if, in addition to feeding from a first side and smoothing from a second side of the carrier material, feeding also occurs from the second side and, in some circumstances, smoothing from the first side.

An extremely thin, self-supporting test field material has especially practical importance in relation to test carriers in which the sample (especially whole blood) is placed on one side of the test field material and a resulting colour reaction is observed on the other side of the test field material. The reagent film mass preferably contains a colour formation reagent and a pigment. With a view to an adequate sample fluid transparency necessary for such applications, it is advantageous if a dispersion film former (instead of a dissolved film former) is used.

Details regarding preferred reagent film masses and the advantages achieved with them can be found in German patent application P 41 06 293.0, to which reference is made.

In the embodiment shown in FIG. 3, the reagent film mass 6 is fed from above. The carrier material ribbon 1 is guided in the direction of arrow 2 over a doctor block 13. Near the end of the doctor block (referred to the transport direction 2), located above the material strip 1 is a doctor box 15 which in the transport direction is closed by a doctor (the name "doctor blade" is also commonly used) and filled with reagent film mass 6. In this case, the top side of the carrier material ribbon 1 is the application side 1a and contacts the lower surface (doctor surface) of doctor 16 from below. In this arrangement, there is preferably used as the smoothing tool—as shown—a second doctor 14, over which the carrier material ribbon 1 is guided (so that the doctor surface of the doctor 14 contacts the carrier material ribbon from below). Here, the sharp edge 14a of doctor 14 should in the transport direction 2 preferably follow a course flush with the sharp edge 16a of doctor 16.

According to an alternative, though by comparison with FIG. 3 less preferable, embodiment, the doctor stone 13 can also serve as a smoothing tool. In this case its edge rearward in the transport direction 2, over which the carrier material ribbon 1 travels, should in the transport direction be located just behind the doctor box 15 and preferably follow a course flush with the sharp edge 16a of the doctor 16.

With this arrangement self-metering is achieved, the metering rate at which the reagent film mass 6 is introduced into the carrier material ribbon 1 being adjustable via the size of the doctor gap, that is, the distance between the lower edge of the doctor 16 and the doctor stone 14. Since the volume of doctor box 15 is confined on the outlet side by doctor 16, the excess of reagent film mass wiped off by the doctor remains in doctor box 15.

FIGS. 4 and 5 show in cross-section a test field material in which a reagent film mass 6 is embedded in a composite fibre structure 19. The threads 20 of the composite fibre structure 19 are preferably thin (maximum thickness 0.1 mm preferably 0.02 to 0.06 mm) and are preferably monofilamentous.

The reagent film mass 6 is applied so that the pores 21 of the composite fibre structure 19 are practically completely filled and the threads 20 are thinly covered with reagent film mass on both sides. The state of the moist carrier material ribbon 10 after smoothing is shown in highly diagrammatic form in FIG. 4.

Due to the drying process the layer thickness of the reagent film mass is reduced. This gives rise to a characteristic structure, in which the surface of the test layer between the threads is slightly concavely curved, as indicated in FIG. 2.

The test material according to the invention is preferably used without any other test layers as a self-supporting test field. Such a test carrier 23 is shown in FIG. 5, the test field 22 being surrounded by a frame 24.

FIG. 6 shows a typical structure of a monofilamentous tissue suitable for the invention. The threads have a loose, lattice-like arrangement with open pores 21. The pore size A should be between 0.02 and 0.08 mm, preferably between 0.03 and 0.05 mm. In the case of square pores shown, the term "pore size" signifies their edge length. With the use of a pore shape diverging from the square shape, the pore size is defined as the square root of the mean pore cross-section.

The thickness B of the threads from which the fibre structure is formed is, as mentioned, preferably between 0.02 and 0.06 mm, values between 0.003 and 0.04 mm being especially preferred. Polyester, for example, has proved successful as thread material. However, other materials are also suitable.

We claim:

1. A method for manufacturing a self-supporting test field material, said method comprising the steps of:
    providing a reagent film mass, said reagent film mass including at least one reagent for performing an analysis of a liquid sample;
    providing a carrier material comprising an open-pored fibre structure, and having a thickness of less than 0.1 mm;
    pressing said reagent film mass into a first side of said carrier material wherein said reagent film mass substantially penetrates into pores of the open-pored fibre structure of the carrier material and wherein a portion of said reagent film mass penetrates through from the first side of the carrier material to a second side of the carrier material;
    smoothing the reagent film mass on the second side of the carrier material by a relative motion of the carrier material and a smoothing tool wherein said pores are substantially filled by the reagent film mass wherein a resulting thickness of the test field material is less than 0.1 mm, and wherein the reagent film mass is distributed essentially symmetrically through the test field material; and
    drying the carrier material in a non-contact manner.

2. Method according to claim 1, wherein the carrier material is a single-layer woven fabric which preferably consists of monofilamentous threads.

3. Method according to claim 1, wherein a viscosity of the reagent film mass during pressing into the carrier material is between 10 mPasec and 300 mPasec.

4. Method according to claim 1, wherein the reagent film mass contains a colour-forming reagent and a pigment.

5. Method according to claim 1, wherein the reagent film mass includes a dispersion film former.

6. Method according to claim 1, wherein the smoothing tool has an edge at its end rearward in a transport direction.

7. A method for manufacturing a self-supporting test field material as recited in claim 1, further comprising the step of metering said reagent film mass applied to said carrier material such that no excess reagent film mass is removed from the carrier material during said smoothing step.

8. A method as recited in claim 1, wherein said first side upon which said reagent film mass is applied is an upper side of the carrier material, said reagent film mass being applied from a doctor box which includes a doctor at a rear portion thereof with respect to a transport direction of the carrier material, said doctor contacting the carrying material thereby performing a smoothing of said upper side, and wherein a smoothing tool contacts said carrier material from a bottom surface, thereby smoothing said first side and said second side.

9. Method according to claim 8, wherein the smoothing tool includes a sharp edge which in a transport direction follows a course flush with a sharp edge of the doctor of the doctor box.

10. A method of manufacturing according to claim 1, further comprising the steps of guiding said carrier material over a slit orifice, wherein said reagent film mass is applied through said slit orifice to said first side of said carrier material, said first side being a bottom surface thereof, said carrier material then being subjected to said smoothing step.

11. A method according to claim 1, wherein the carrier material is a single layer knitted fabric which consists of monofilamentous threads.

12. A method according to claim 1, wherein a viscosity of the reagent film mass during pressing into the carrier material is between 20 mPasec and 200 mPasec.

13. A self-supporting test field material for a test carrier for the determination of an analyte in a body fluid, said test field material comprising:
a reagent film mass embedded in an open-pored fibre structure (19) wherein said reagent film mass spans and thus closes pores of said open-pored fibre structure, the reagent film mass including at least one reagent of an analysis reagent system and a polymer film former, said reagent film mass being pressed into the composite fibre structure and smoothed on first and second sides thereof, such that said test field material has substantially smooth first and second sides, and wherein a mean thickness of said test field material is less than 0.1 mm.

14. Test field material according to claim 11, wherein an average pore size of the fibre structure is between 0.02 mm and 0.08 mm.

15. Test field material according to claim 13, wherein a mean thickness of said test field material is less than 0.07 mm.

16. Test field material according to claim 13, wherein an average pore size of the fibre structure is between 0.03 and 0.05 mm.

17. A self-supporting test field material for a test carrier for the determination of an analyte in a body fluid, said test field material comprising:
an open-pored fibre structure of a single layer fabric having pores with an average pore size between 0.02 and 0.08 mm;
a reagent film mass disposed upon and pressed through said fibre structure, wherein said reagent film mass spans and closes the pores of said fibre structure, said reagent film mass containing at least one reagent of an analysis reagent system and a polymer film former,
wherein said reagent film mass is pressed into the fibre structure and smoothed on first and second sides thereof, such that the single layer fabric is covered by a thin layer of said reagent film mass wherein said test field material has a thickness of less than 0.1 mm and wherein the test field material has substantially smooth first and second sides which correspond to the first and second sides of the fibre structure.

18. A test field material as recited in claim 17, wherein said single layer fabric is a woven single layer fabric.

19. A test field material as recited in claim 17, wherein single layer fabric is a knitted fabric.

* * * * *